(12) United States Patent
Brandner et al.

(10) Patent No.: US 11,278,342 B2
(45) Date of Patent: Mar. 22, 2022

(54) MEDICAL DEVICES UTILIZING SHAPE MEMORY ALLOYS AND ASSOCIATED SYSTEMS AND METHODS

(71) Applicants: Theresa Brandner, San Francisco, CA (US); Susannah Wedgwood, San Francisco, CA (US)

(72) Inventors: Theresa Brandner, San Francisco, CA (US); Susannah Wedgwood, San Francisco, CA (US)

( * ) Notice: Subject to any disclaimer, the term of this patent is extended or adjusted under 35 U.S.C. 154(b) by 611 days.

(21) Appl. No.: 15/488,352

(22) Filed: Apr. 14, 2017

(65) Prior Publication Data
US 2017/0296253 A1 Oct. 19, 2017

Related U.S. Application Data

(60) Provisional application No. 62/322,689, filed on Apr. 14, 2016.

(51) Int. Cl.
*A61B 18/04* (2006.01)
*A61L 31/02* (2006.01)
(Continued)

(52) U.S. Cl.
CPC .......... *A61B 18/04* (2013.01); *A61B 18/1482* (2013.01); *A61B 18/1492* (2013.01); *A61L 31/022* (2013.01); *A61B 2018/00095* (2013.01); *A61B 2018/00488* (2013.01); *A61B 2018/00494* (2013.01); *A61B 2018/00559* (2013.01);
(Continued)

(58) Field of Classification Search
CPC . A61B 18/04; A61B 18/1482; A61B 18/1492; A61B 2018/00095; A61B 2018/00488; A61B 2018/00494; A61B 2018/00559; A61B 2018/00601;
(Continued)

(56) References Cited

U.S. PATENT DOCUMENTS 5,201,741 A 4/1993 Dulebohn
5,437,665 A 8/1995 Munro
(Continued)

FOREIGN PATENT DOCUMENTS

WO 2005096967 A2 10/2005
WO 2012103157 A1 8/2012

OTHER PUBLICATIONS

Di Spiezio Sardo et al., Hysteroscopic myomectomy: a comprehensive review of surgical techniques, Human Reproduction Update, vol. 14, No. 2, pp. 101-119, 2008.
(Continued)

*Primary Examiner* — Michael F Peffley
(74) *Attorney, Agent, or Firm* — Fortem IP LLP; Katrina Marcelo; Mary Fox

(57) ABSTRACT

Medical devices utilizing shape memory alloys and associated methods are disclosed herein. One aspect of the present technology, for example, is directed toward a treatment element configured to be positioned within a body lumen and coupled to an energy source. At least a portion of the treatment element may be made of a shape memory alloy, and wherein application of thermal energy to the treatment element from the energy source transforms the treatment element from the martensitic state to the austenitic state in which the treatment element is configured to cut, ablate, resect, and/or cauterize tissue.

18 Claims, 7 Drawing Sheets

(51) Int. Cl.
  *A61B 18/14* (2006.01)
  *A61B 18/00* (2006.01)

(52) U.S. Cl.
  CPC .............. *A61B 2018/00601* (2013.01); *A61B 2018/1407* (2013.01); *A61F 2210/0014* (2013.01); *A61F 2250/0042* (2013.01); *A61L 2400/16* (2013.01)

(58) Field of Classification Search
  CPC ........... A61B 2018/1407; A61L 31/022; A61L 2400/16; A61F 2210/0014; A61F 2250/0042
  See application file for complete search history.

(56) References Cited

U.S. PATENT DOCUMENTS

| | | | |
|---|---|---|---|
| 5,611,803 A * | 3/1997 | Heaven | A61B 17/00234 606/110 |
| 5,749,870 A | 5/1998 | Gloth et al. | |
| 5,980,517 A | 11/1999 | Gough | |
| 5,980,519 A | 11/1999 | Hahnen et al. | |
| 6,071,280 A | 6/2000 | Edwards et al. | |
| 6,113,597 A | 9/2000 | Eggers et al. | |
| 6,306,141 B1 | 10/2001 | Jervis | |
| 6,375,668 B1 | 4/2002 | Gifford et al. | |
| 6,416,545 B1 | 7/2002 | Mikus et al. | |
| 6,645,199 B1 * | 11/2003 | Jenkins | A61B 18/1492 606/41 |
| 7,229,440 B2 | 6/2007 | Ho et al. | |
| 7,335,197 B2 | 2/2008 | Sage et al. | |
| 7,918,795 B2 | 4/2011 | Grossman | |
| 8,157,797 B2 | 4/2012 | Boukhny et al. | |
| 8,343,167 B2 | 1/2013 | Henson | |
| 8,777,939 B2 | 7/2014 | Lee et al. | |
| 8,790,281 B2 | 7/2014 | Diederich et al. | |
| 2001/0051802 A1 | 12/2001 | Woloszko et al. | |
| 2002/0193781 A1 | 12/2002 | Loeb | |
| 2005/0131508 A1 | 6/2005 | Garabedian et al. | |
| 2007/0088369 A1 | 4/2007 | Shaw et al. | |
| 2012/0116382 A1 | 5/2012 | Ku et al. | |
| 2012/0123531 A1 * | 5/2012 | Tsukashima | A61F 2/2448 623/2.37 |
| 2012/0197246 A1 | 8/2012 | Mauch | |
| 2013/0178910 A1 * | 7/2013 | Azamian | A61B 17/00234 607/33 |
| 2014/0276755 A1 * | 9/2014 | Cao | A61B 18/1492 606/33 |
| 2014/0276764 A1 * | 9/2014 | Shuman | A61B 18/1492 606/34 |
| 2015/0018727 A1 | 1/2015 | Diederich et al. | |

OTHER PUBLICATIONS

International Search Report and Written Opinion dated Sep. 12, 2017; International Application No. PCT/US2017/027805; 19 pages.
Petrini et al., Biomedical Applications of Shape Memory Alloys, Journal of Metallurgy, vol. 2011, Article ID 601483, 15 pages.
Nitinol, Fort Wayne Metals Research Corp., https://www.fwmetals.com/materials/nitinol/, 2019.

* cited by examiner

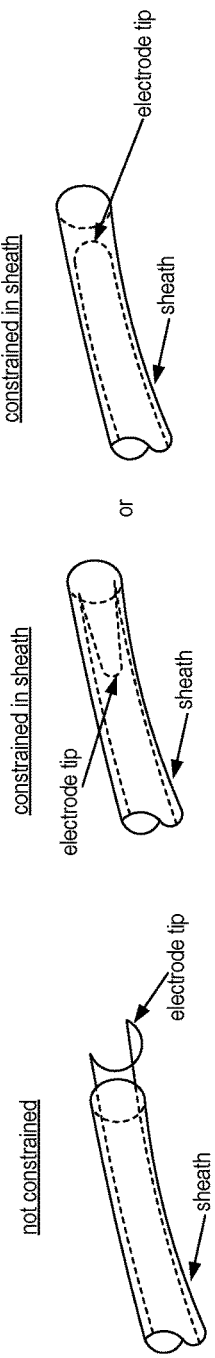
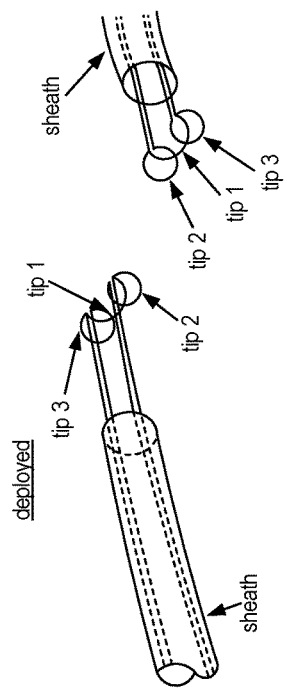
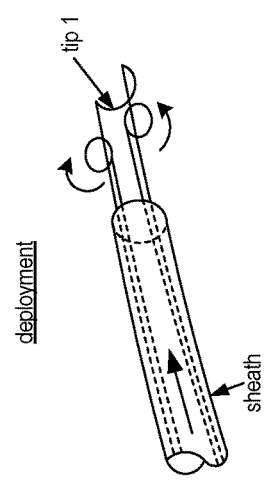
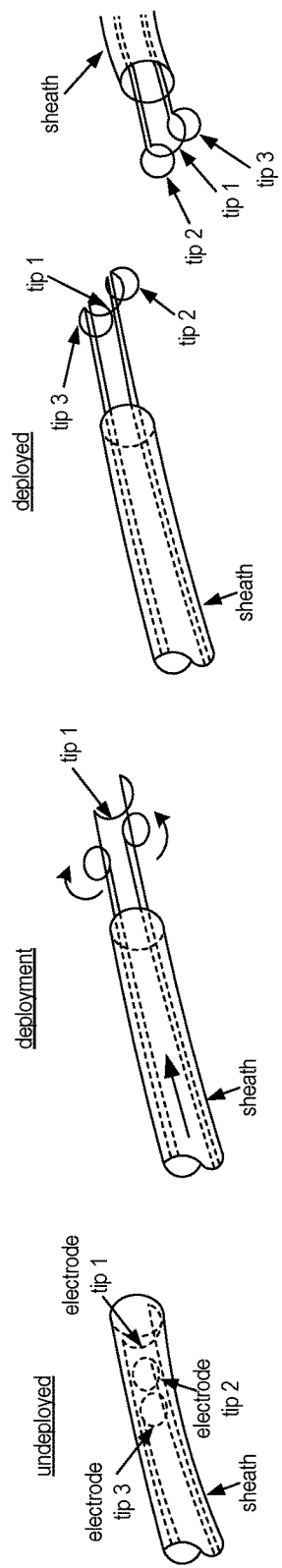
FIG. 1A   FIG. 1B   FIG. 1C
FIG. 2A   FIG. 2B   FIG. 2C

MEDICAL DEVICES UTILIZING SHAPE MEMORY ALLOYS AND ASSOCIATED SYSTEMS AND METHODS

RELATED APPLICATION

This application claims the benefit of U.S. Provisional Application No. 62/322,689, filed Apr. 14, 2016, entitled "MEDICAL DEVICES UTILIZING SHAPE MEMORY ALLOYS AND ASSOCIATED SYSTEMS AND METHOD," which is incorporated by reference herein in its entirety.

TECHNICAL FIELD

The present technology is directed generally to medical devices utilizing shape memory alloys and associated systems and methods.

BACKGROUND

A shape memory alloy ("SMA") is a metallic alloy that undergoes a phase transformation in its crystal structure when cooled from its stronger, high temperature form (austenite or parent) to its easily deformable, low temperature form (martensite or daughter). This inherent phase transformation is the basis for the unique properties of SMAs, such as shape memory and superelasticity.

Shape memory refers to the ability of an SMA to go through the following process: (1) While in its martensitic form, the SMA is (easily) deformed to a new shape. (2) Upon being heated through its transformation temperatures, the SMA reverts to austenite and recovers its previous shape (before the deformation) with great force. The temperature at which the SMA remembers its austenite form when heated can be adjusted by slight changes in alloy composition and through heat treatment. Various medical device applications include an SMA component and utilize its shape memory properties to selectively transform the component between two different shapes or configurations. Such SMA components typically have an austenitic phase that is activated at a transition temperature typically at or below body temperature. (Note: body temperature is documented in medical textbooks as 37° C., but it is reported to range between 36.1° C. to 38° C.) Examples of such devices include dental wire, intravascular stents, guidewires, embolic coils, as well as staples, vertebral spacers, intrauterine devices, catheters, cannulas, and minimally invasive surgical instruments.

Superelasticity is a mechanical version of shape memory, and is caused by the stress-induced formation of some martensite above its normal temperature. Because it has been formed above its normal temperature, the martensite reverts immediately to undeformed austenite as soon as the stress is removed. This process provides a very springy, "rubberlike" elasticity in these alloys. The superelastic properties of SMAs have been employed in various medical device applications where it is advantageous for the device to spring to form. Some examples of such devices include orthodontic wire, venous filters, vascular stents, and minimally invasive surgical instruments.

BRIEF DESCRIPTION OF THE DRAWINGS

FIG. 1A is a schematic, perspective view of a distal portion of a medical device showing a treatment element in an unconstrained austenitic state in accordance with the present technology.

FIG. 1B is a schematic, perspective view of the treatment element shown in FIG. 1A bent back on itself in a low-profile martensitic state in a delivery sheath in accordance with the present technology.

FIG. 1C is a schematic, perspective view of the treatment element shown in FIG. 1A in an elongated low-profile martensitic state in a delivery sheath in accordance with the present technology.

FIG. 2A is a schematic, perspective view of a distal portion of a medical device showing a treatment element in an unconstrained austenitic state in accordance with the present technology.

FIG. 2B is a schematic, perspective view of the treatment element shown in FIG. 1A bent back on itself in a low-profile martensitic state in a delivery sheath in accordance with the present technology.

FIG. 2C is a schematic, perspective view of the treatment element shown in FIG. 1A in an elongated low-profile martensitic state in a delivery sheath in accordance with the present technology.

DETAILED DESCRIPTION

Figure 3A:
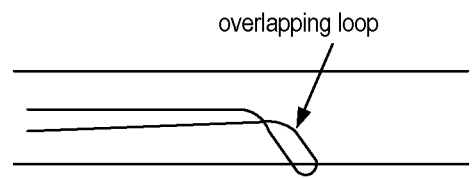
FIGS. 3A-3C are side, top, and perspective views, respectively, of a treatment element in accordance with the present technology.

The present technology is directed generally to shape memory treatment devices and associated systems and methods. In particular embodiments of the present technology, the treatment device includes a treatment element (e.g., an electrode or other device) configured to be delivered to a treatment site within a body cavity or lumen or other natural body orifice via a delivery device (e.g., a trocar, venipuncture, through a device lumen, etc.). The electrode is made of an SMA and is transformable between a delivery configuration and a deployed configuration via thermal activation. In the delivery configuration, the electrode is in its martensitic form and can be constrained for delivery through a delivery device and/or through narrow or tortuous bodily passages. In the deployed configuration, the electrode is in an austenitic form that is configured to treat, manipulate, or otherwise engage bodily tissue at the treatment site. For example, the shape and/or temperature of the electrode in the austenitic form can be configured for object retrieval, thrombus retrieval, tissue biopsy, tissue manipulation, and/or the atherectomy, morcellation, liquification, denaturation, dessication, fulgaration, cauterization, vaporization, cutting, and/or ablation of target tissue in minimally invasive and surgical applications. The electrode can be thermally activated to its austenitic form at a transition temperature above 40° C. (above body temperature). The electrode is coupled to an energy source, and activation of the austenitic phase of the electrode is achieved through use of heat energy and/or electrical current. Suitable energy sources include, for example, direct current (DC), alternating current (AC), radio frequency (RF), magnetic energy, electromagnetic energy, an electrical current transformed to mechanical energy via an ultrasonic transducer, thermal transfer (via fluidic heat exchange), and others.

The electrode can be made of an SMA that is selected based on the desired physical characteristics and performance parameters of the particular device. Suitable SMAs include, for example, nickel titanium ("NiTi" or "nitinol"), platinum ("Pt"), platinum-titanium-nickel ("PtTiNi"), platinum iron ("PtFe"), copper-zinc-aluminum ("CuZnAl"), copper-aluminum-nickel ("CuAlNi"), and/or other alloys of/with platinum, nickel, iron, copper, titanium, etc.

As detailed below, the treatment devices and/or electrodes of the present technology are configured for use in one or more medical applications and/or fields of medicine, such as gynecology, urology, cardiovascular, neurovascular, peripheral vascular, laparoscopy, pulmonology, ENT applications, and gastroenterology. Although the following description pertains to gynecological, urological, cardiovascular, and neurological applications of the present technology, additional medical applications and/or treatment methods are also within the scope of the present technology.

Selected Embodiments of Treatment Devices for Use in Gynecological Applications

Modern advances in minimally invasive surgical methods have improved outcomes and reduced complications and recovery times for many types of surgery. In some cases, minimally invasive techniques have made it possible to move surgical procedures out of the operating room and into a doctor's office setting. In the area of women's health, however, minimally invasive advancements are scant, especially as it relates to transcervical hysteroscopic surgery. For example, many hysteroscopic surgical methods today require hysteroscopes having relatively large diameters, e.g., 26 Fr (8 mm), thus necessitating the use of uncomfortable luminaria dilatation, or anesthesia and manual cervical dilation in an operating room setting.

Figure 3B:
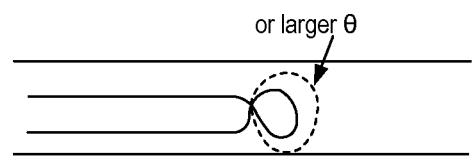
Figure 3C:
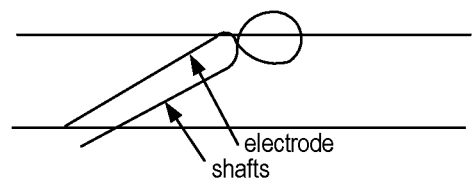
Figure 3D:
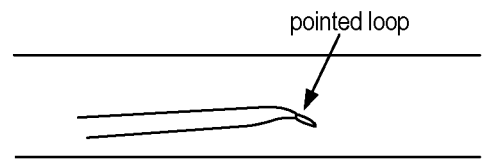
FIGS. 3D-3F are side, top, and perspective views, respectively, of a treatment element in accordance with the present technology.
Figure 3E:
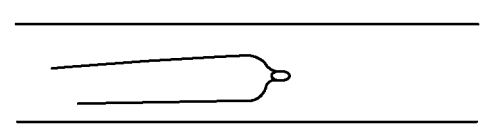
Figure 3F:
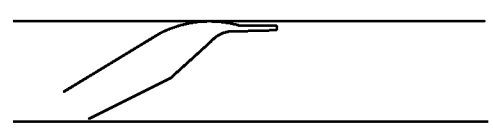
Figure 3G:
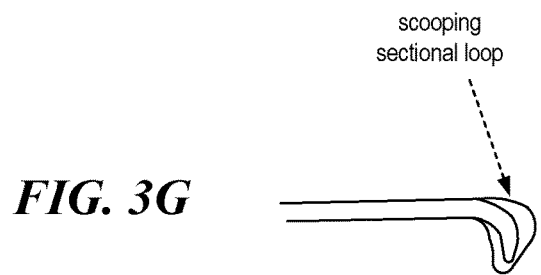
FIGS. 3G-3I are side, top, and perspective views, respectively, of a treatment element in accordance with the present technology.
Figure 3H:
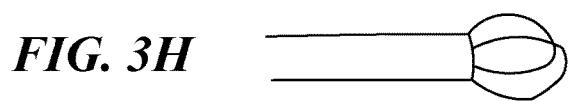
Figure 3I:
Figure 3J:
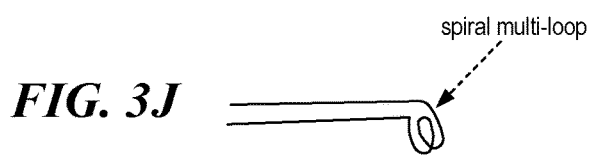
FIGS. 3J-3L are side, top, and perspective views, respectively, of a treatment element in accordance with the present technology.
Figure 3K:
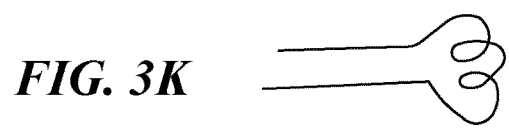
Figure 3L:
Figure 4A:
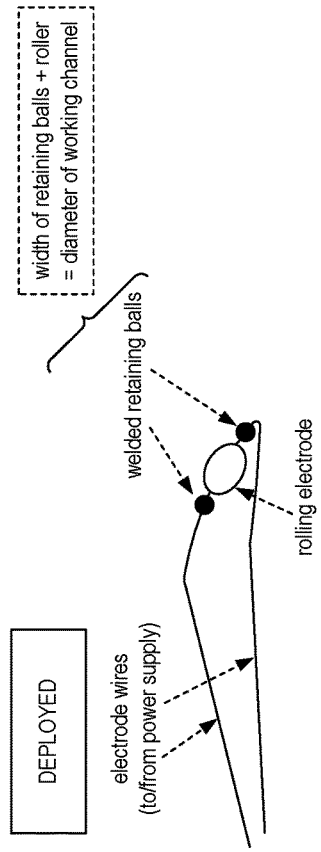
FIGS. 4A and 4B are schematic illustrations of a treatment element in a deployed state and a constrained state in accordance with the present technology.
Figure 4B:
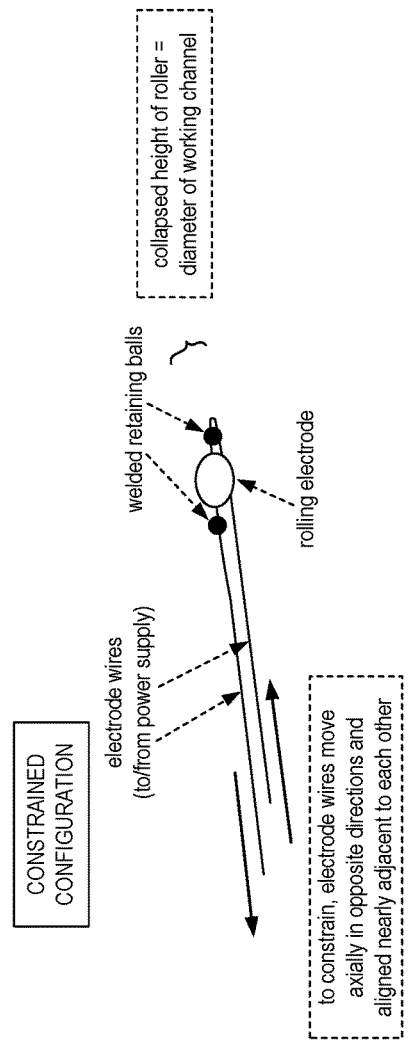
Figure 5A:
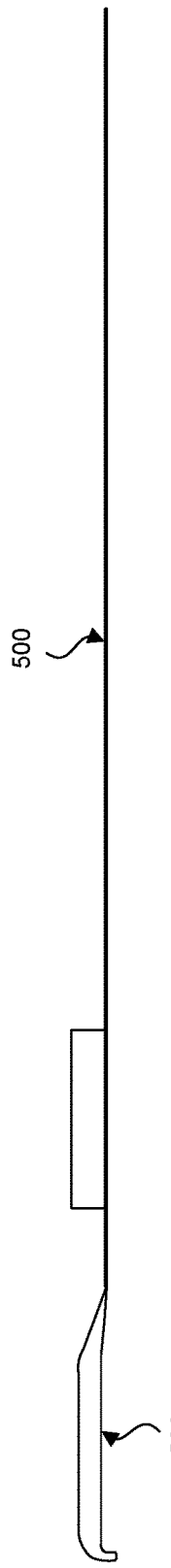
FIG. 5A is a side view of a manipulation member having a looped treatment element at its distal portion in accordance with the present technology.
Figure 5D:
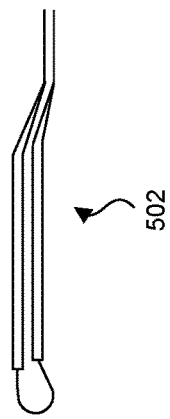
FIGS. 5B-5D and FIGS. 6A-6C are side views and perspective side views, respectively, of treatment elements having different angles at their distal portions in the austenitic state in accordance with the present technology.
Figure 5C:
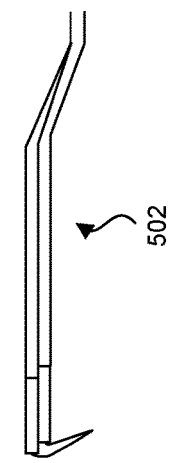
Figure 5B:
Figure 6A:
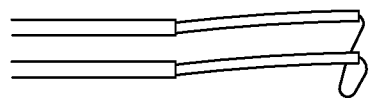
Figure 6B:
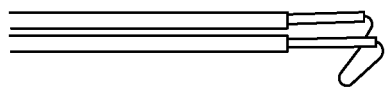
Figure 6C:
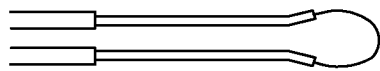
Figure 7A:
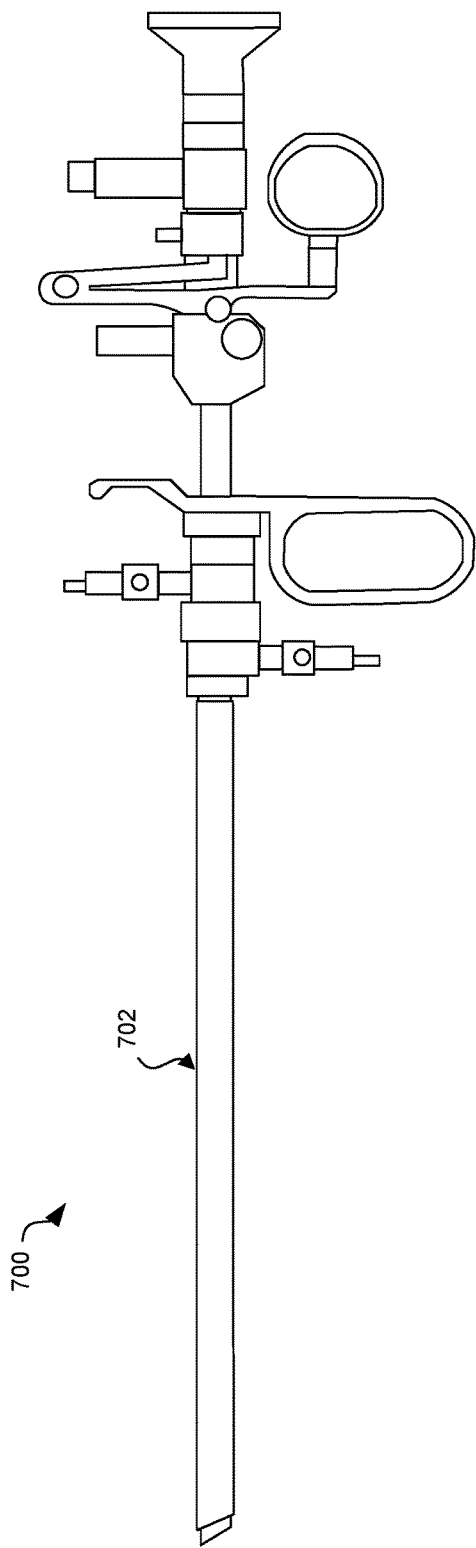
FIG. 7A is a side view of a hysteroscopic resectoscope configured for use with the treatment elements of the present technology.
Figure 7B:
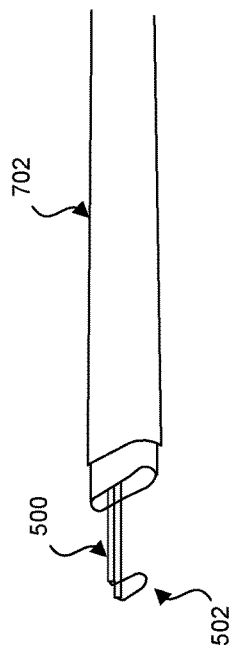
FIG. 7B is an enlarged view of a distal portion of the hysteroscopic resectoscope shown in FIG. 7A.

One embodiment of the present technology configured for gynecological applications includes a cutting electrode having a single or multiple loop configuration during use. At least a portion of the electrode can be formed of an SMA (such as NiTi or PtTiNi). Representative embodiments of the electrode and/or associated systems and methods are shown in FIGS. 1A-7B. The electrode is configured to be delivered in fluid medium to a uterine cavity through a lumen of a delivery device, such as the working channel of a hysteroscopic resectoscope (FIGS. 7A and 7B) or other delivery device having a lumen that is 8 mm or less. During delivery to the uterine cavity, the electrode can be compacted into a compressed martensitic shape to fit within the lumen of the delivery device. The electrode can be electrically connected to an energy source.

Once positioned at or near a treatment site (e.g., myoma) within the uterine cavity, the energy source can be electrode can be activated into the austenitic phase to form an expanded, pre-set shape (i.e., wider than the inner diameter of the delivery device lumen). In some embodiments, for example, the electrode can be activated via radiofrequency energy (RF) (e.g., from about 100 kHz to about 5 MHz). When the electrode is in the deployed, pre-set shape, the electrode is configured to perform one or more procedures at the treatment site, such as cutting, ablating, resecting, manipulating, and/or cauterizing tissue such as leiomyoma, endometrium, or other tissue. At any time before, during, and/or after treatment, but before removing the electrode from the uterine cavity, the energy source can be de-activated or otherwise decoupled from the electrode such that the electrode temperature equilibrates (under fluid medium or ambient tissue temperature) to the martensitic phase. Once in the martensitic phase, the device can be withdrawn from the uterine cavity through the delivery device.

Another embodiment of the present technology configured for gynecological applications is an ultrasonic surgical tip including an SMA (such as NiTi or PtTiNi). Representative embodiments of the electrode and/or associated systems and methods are shown in FIGS. 1-3. The tip is configured to be introduced in a straight martensitic form through a lumen of a delivery device (such as the working channel of a hysteroscope or other delivery device having an outer diameter of 3 mm or less (9F)). Once positioned at or near the treatment site in the uterine cavity, the tip can be thermally activated into its austenitic phase using ultrasonic energy (e.g., from about 27 kHz to about 75 kHz). In the austenitic phase, the tip has a pre-set bend that serves as the stroke length of the ultrasonic surgical tip, and is subsequently used for denaturization, cauterization, ablation, fractionation, and/or morcellation of leiomyoma or other tissue. Upon removal of energy input, the surgical tip temperature equilibrates under fluid medium to the martensitic phase, and is retrieved through working channel. This device may be used in conjunction with fluid management and aspiration to facilitate the removal of excised, morcellated, and/or fractionated material.

Selected Embodiments of Treatment Devices for Use in Gynecological/Urological Applications Another embodiment of the present technology includes a nitinol grasping trap or claw shape that is encapsulated in an insulative coating, thus preventing or substantially preventing thermal transfer to tissue, and constrained into a compressed "grasping" martensitic shape, delivered under fluid medium through the working channel of a cystoscope, ureteroscope, hysteroscope, cannula, catheter, or other lumen, through a narrow or tortuous bodily passage, and into a cavity or space such as within the bladder, kidney, uterus, urethra, ureter, or prostate, and activated (e.g., thermally) into the austenitic phase at transition temperature (around 80° C.) to form a remembered 'open' shape that is larger in diameter or different in shape than the inner diameter of the channel or lumen, and is subsequently used to enclose, grasp, and thus capture an object, embolus, tissue or material, and the subsequent removal of energy input causes the claw to cool within the fluid medium to regain a grasping martensitic shape, at which point the claw is removed through the lumen along with the retrieved object or material. (FIG. 1, FIG. 3)

Another embodiment of this technology is a nitinol grasping trap or claw shape, encapsulated in an insulative coating thus completely preventing thermal/energy transfer to tissue, and shape set to remember a constricted 'grasping' austenitic shape. This device is compressed and delivered via the working channel of a cystoscope, ureteroscope, hysteroscope, cannula, catheter, or other lumen, through a narrow or tortuous bodily passage, and into a cavity or space such as within the bladder, kidney, uterus, urethra, ureter, or prostate, and released from constraint to form an 'open' martensitic shape, at body or ambient fluid temperature, that is larger in diameter or different in shape than the inner diameter of the channel or lumen. The device is then used to enclose, grasp, and thus capture an object or material, and subsequently activated (heated liquid through a lumen or low direct current) into the austenitic phase at transition temperature (around 60° C.) to form the remembered shape and remain in the austenitic 'grasping shape' (the force may produce a stronger grasp than embodiment #3) and thus capture an object, embolus, tissue, or material, at which point, while remaining in its austenitic grasping phase, the claw is removed through the lumen along with the retrieved object or material. (FIG. 3)

Selected Embodiments of Treatment Devices for Use in Cardiovascular Applications Another embodiment of this technology is a PtTiNi cutting electrode or probe composed of a single wire or multi wire loop or tube or scoop shape or other shape that can be collapsed into a compressed martensitic shape and delivered through a cannula or catheter or other lumen and then activated into the austenitic phase to resume a pre-formed shape that is larger in diameter than the inner diameter of the channel or lumen, and which is subsequently used to perform cutting, ablation (e.g., super ventricular tachycardia), biopsy, resection, removal, manipulation, and cautery of heart valves, chordae tendinae, cardiac tissue, vascular tissue, other adjacent tissue, or other material. Upon removal or reduction of energy input, the electrode or probe temperature equilibrates under fluid medium or ambient tissue temperature to the martensitic phase, and is retrieved through the cannula or catheter or other lumen and may contain a sample of tissue, calcification, atherogenic/atheromatous, fibrous, thrombotic, embolic, or other material or substance. (FIG. 1, FIG. 2, FIG. 3)

Selected Embodiments of Treatment Devices for Use in Neurological Applications Another embodiment of this technology is a PtFe cutting electrode or probe composed of a single wire or multi wire loop or tube or scoop shape or other shape that can be collapsed into a compressed martensitic shape and delivered through a cannula or catheter or other lumen and then magnetically activated into the austenitic phase to resume a pre-formed shape that is larger in diameter than the inner diameter of the channel or lumen, and which is subsequently used to perform cutting, ablation, biopsy, removal, manipulation, dissolution, liquification, and cautery, of an atherosclerotic or thrombotic lesion or other unwanted tissue. Upon removal or reduction of energy input, the electrode or probe temperature equilibrates under fluid or ambient blood temperature to the martensitic phase, and is retrieved through the cannula or catheter or other lumen and may contain a sample of tissue, calcification, atherogenic/atheromatous, fibrous, thrombotic, embolic, or other material or substance. (FIG. 1, FIG. 2, FIG. 3)

Additional Embodiments

The treatment devices and/or electrodes of the present technology use the shape memory phase (of the SMA that forms the electrode) for or during the treatment or therapeutic functioning of the device unlike many other devices that do not use the shape memory phase (and actually use only the superelastic phase) for or during the actual treatment or therapeutic functioning of the device.

In some embodiments, the treatment device and/or electrode utilizes both the superelastic and shape memory properties of the SMA.

In some embodiments, the treatment devices and/or electrodes of the present technology use the austenite to martensite phase transformation as part of the treatment or therapeutic functioning of the device.

In some embodiments of the treatment devices and/or electrodes of the present technology, the treatment device and/or electrode can be compressed to fit through the delivery device lumen or opening in a manner that involves more or significantly more material strain compression than devices that employ superelasticity.

The treatment devices and/or electrodes of the present technology provide the following advantages over conventional SMA electrodes: (1) the deployed shapes of the electrodes of the present technology are relatively larger than those of other conventional designs and thus can remove more tissue, (2) the SMA forming the electrodes of the present technology have an $A_f$ temperature that produces a stronger peak force than devices that rely solely on superelasticity.

Ultrasound, radiofrequency, magnetics, and/or conductive heat can be used to activate the shape memory properties of the electrodes of the present technology.

In some embodiments of the treatment devices and/or electrodes disclosed herein, the treatment device and/or electrode removes tissue and liquifies the tissue using mechanical (ultrasonic) energy.

In some embodiments of the treatment devices and/or electrodes disclosed herein, at least a portion of the electrode and/or treatment device includes an SMA that demonstrate superelastic properties but does not revert/reverse to the martensitic phase after being activated in the austenitic phase.

EXAMPLES

The following examples are illustrative of several embodiments of the present technology:

1. A device for removing tissue from a body lumen, the device comprising:
   a delivery shaft having a lumen therethrough;
   an energy source;
   a manipulation member configured to be slidably received through the lumen of the delivery shaft, wherein the manipulation member has a distal portion configured to be positioned within the body lumen; and
   a treatment element at the distal portion of the manipulation member and coupled to the energy source, at least a portion of the treatment element made of a shape memory alloy and having a low-profile martensitic state for delivery through the elongated shaft and an expanded, austenitic state that forms a pre-set shape having a cross-sectional dimension that is greater than the cross-sectional dimension of the shaft, and wherein application of thermal energy to the treatment element from the energy source transforms the treatment element from the martensitic state to the austenitic state, and wherein, when the treatment element is in the austenitic state, the treatment element is configured to cut, ablate, resect, and/or cauterize tissue.

2. The device of example 1, wherein the treatment element transforms from the martensitic state to the austenitic state at a temperature above 40 degrees Celsius.

3. The device of example 1 or example 2, wherein the energy source is configured to deliver radiofrequency energy to the treatment element.

4. The device of any one of examples 1-3, wherein the treatment element is thermally activated and transforms from the martensitic state at a frequency of from about 100 kHz to about 5 MHz.

5. The device of any one of examples 1-4, wherein the distal portion of the manipulation member is configured to be delivered to a uterine cavity.

6. The device of example 5, wherein the device is configured to separate a tumor from the uterine cavity.

7. The device of any one of examples 1-6, wherein the treatment element has a single loop configuration.

8. The device of any one of examples 1-6, wherein the treatment element has a multiple loop configuration.

9. The device of any one of example 1-8, wherein the delivery shaft is a portion of a hysteroscopic resectoscope.

10. The device of any one of examples 1-9, wherein the delivery shaft includes a fluid medium within the lumen.

11. The device of any one of examples 1-10, wherein a cross-sectional dimension of the delivery shaft is no more than 8 mm.

12. The device of any one of examples 1-11, wherein the tissue is at least one of a leiomyoma and endometrium.

13. A device for removing tissue from a body lumen, the device comprising:
    a delivery shaft having a lumen therethrough;
    an energy source;
    a manipulation member configured to be slidably received through the lumen of the delivery shaft, wherein the manipulation member has a distal portion configured to be positioned within the body lumen; and
    a treatment element at the distal portion of the manipulation member and coupled to the energy source, at least a portion of the electrode made of a shape memory alloy and having a low-profile martensitic state for delivery through the elongated shaft and an expanded, austenitic state that forms a pre-set shape having a cross-sectional dimension that is greater than the cross-sectional dimension of the shaft, and
    wherein application of ultrasonic energy to the treatment element from the energy source transforms the treatment element from the martensitic state to the austenitic state, and
    wherein, when the treatment element is in the austenitic state, the electrode is configured to cut, ablate, resect, morcellate, and/or cauterize tissue comprising at least one of leiomyoma and endometrium.

14. The device of example 13, wherein the treatment element transforms from the martensitic state to the austenitic state at a frequency of from about 27 kHz to about 75 kHz.

15. The device of example 13 or example 14, wherein the energy source is configured to deliver ultrasonic energy to the treatment element.

16. The device of any one of examples 13-15, wherein the treatment element is generally straight in a martensitic state and bent in an austenitic state.

17. The device of any one of examples 13-16, wherein the distal portion of the manipulation member is configured to be delivered to a uterine cavity.

18. The device of any one of examples 13-17, wherein the device is configured to separate a tumor from the uterine cavity.

19. The device of any one of examples 13-18, wherein the treatment element has a single loop configuration.

20. The device of any one of examples 13-18, wherein the treatment element has a multiple loop configuration.

21. The device of any one of examples 13-20, wherein the delivery shaft is a portion of a hysteroscopic resectoscope.

22. The device of any one of examples 13-21, wherein the lumen of the delivery shaft includes a fluid medium.

23. The device of any one of examples 13-22, wherein a cross-sectional dimension of the delivery shaft is no more than 3 mm.

24. The device of any one of examples 13-23, wherein the tissue is at least one of a leiomyoma and endometrium.

25. A method for modifying and/or treating tissue comprising:
    positioning a treatment element in a low-profile martensitic state within a body lumen via a delivery shaft having a cross-sectional dimension, wherein the treatment element is made of a shape memory alloy;
    while the treatment element is positioned within the body lumen, transforming the treatment element from the martensitic state to the austenitic state by delivering thermal energy to the treatment element, wherein, in the austenitic state the treatment element forms an expanded, pre-set shape having a cross-sectional dimension that is greater than the cross-sectional dimension of the delivery shaft; and
    cutting, ablating, resecting, morcellating, and/or cauterizing tissue within the body lumen with the treatment element in the austenitic state.

26. The method of example 25, wherein delivering thermal energy includes raising a temperature of the treatment element to no greater than 40 degrees Celsius.

27. The method of example 25, wherein the cross-sectional dimension of the delivery shaft is no greater than 8 mm.

28. The method of example 25, wherein transforming the treatment element includes delivering a radiofrequency to the treatment element of from about 100 kHz to about 5 MHz.

29. A method for modifying and/or treating tissue comprising:
    positioning a treatment element in a low-profile martensitic state within a body lumen via a delivery shaft having a cross-sectional dimension, wherein the treatment element is made of a shape memory alloy;
    while the treatment element is positioned within the body lumen, transforming the treatment element from the martensitic state to the austenitic state by delivering ultrasonic energy to the treatment element, wherein, in the austenitic state the treatment element forms an expanded, pre-set shape having a cross-sectional dimension that is greater than the cross-sectional dimension of the delivery shaft; and cutting, ablating, resecting, morcellating, and/or cauterizing tissue within the body lumen with the treatment element in the austenitic state.

30. The method of example 29, wherein the cross-sectional dimension of the delivery shaft is no greater than 3 mm.

31. The method of example 29, wherein transforming the treatment element includes delivering a ultrasonic energy to the treatment element that has a frequency of from about 27 kHz to about 75 kHz.

CONCLUSION

From the foregoing, it will be appreciated that specific embodiments of the disclosed technology have been described herein for purposes of illustration, but that various modifications may be made without deviating from the technology. Certain aspects of the technology described in the context of particular embodiments may be combined or eliminated in other embodiments. Further, while advantages associated with certain embodiments of the disclosed technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for removing tissue from a body lumen, the device comprising:
    a delivery shaft having a lumen therethrough;
    an energy source;
    a manipulation member configured to be slidably received through the lumen of the delivery shaft, wherein the manipulation member has a distal portion configured to be positioned within the body lumen; and
    a treatment element at the distal portion of the manipulation member and coupled to the energy source, the treatment element consisting of a shape memory alloy and having a low-profile martensitic state for delivery through the elongated shaft and an expanded, austenitic state, wherein, in the austenitic state, the treatment element forms a pre-set shape having a cross-sectional dimension that is greater than the cross-sectional dimension of the shaft, wherein the pre-set shape comprises a loop configuration with a pre-set bend, and
    wherein application of thermal energy to the treatment element from the energy source transforms the treatment element from the martensitic state to the austenitic state,
    wherein, when the treatment element is in the austenitic state, the treatment element is configured to directly engage a wall of the body lumen to resect tissue from the wall, and
    wherein the treatment element transforms from the martensitic state to the austenitic state at a temperature above 40 degrees Celsius.

2. The device of claim 1, wherein the energy source is configured to deliver radiofrequency energy to the treatment element.

3. The device of claim 2, wherein the treatment element is thermally activated and transforms from the martensitic state at a frequency of from about 100 kHz to about 5 MHz.

4. The device of claim 1, wherein the distal portion of the manipulation member is configured to be delivered to a uterine cavity.

5. The device of claim 4, wherein the device is configured to separate a tumor from the uterine cavity.

6. The device of claim 1, wherein the treatment element has a single loop configuration.

7. The device of claim 1, wherein the treatment element has a multiple loop configuration.

8. The device of claim 1, wherein the delivery shaft is a portion of a hysteroscopic resectoscope.

9. The device of claim 1, wherein the lumen of the delivery shaft includes a fluid medium.

10. The device of claim 1, wherein a cross-sectional dimension of the delivery shaft is no greater than 8 mm.

11. The device of claim 1, wherein the tissue is at least one of a leiomyoma and endometrium.

12. The device of claim 1, wherein the treatment element has a scoop shape.

13. The device of claim 1, wherein the loop configuration is an open loop configuration.

14. The device of claim 1, wherein, when the treatment element is in the austenitic state, the treatment element is configured to directly engage a wall of the body lumen to cut, ablate, and/or cauterize tissue at the wall of the body lumen.

15. The device of claim 1, wherein the pre-set shape comprises a u-shaped configuration disposed at an angle relative to a longitudinal axis of the manipulation member.

16. A device for treating tissue in a body lumen, the device comprising:
    a delivery shaft having a lumen therethrough;
    an energy source;
    an elongate manipulation member; and
    a treatment element at a distal portion of the manipulation member and consisting of a shape memory alloy having a low-profile martensitic state for delivery through the delivery shaft and an expanded, austenitic state, wherein, in the austenitic state, the treatment element has a pre-set shape having a cross-sectional dimension that is greater than the cross-sectional dimension of the delivery shaft, wherein the pre-set shape comprises a u-shaped configuration disposed at an angle relative to a longitudinal axis of the manipulation member,
    wherein application of thermal energy to the treatment element from the energy source transforms the treatment element from the martensitic state to the austenitic state,
    wherein, when the treatment element is in the austenitic state, the treatment element is configured to directly engage tissue at a wall of the body lumen to cut, ablate, resect, and/or cauterize the tissue, and
    wherein the treatment element transforms from the martensitic state to the austenitic state at a temperature above 40 degrees Celsius.

17. The device of claim 16, wherein, when the treatment element is in the austenitic state, the portion of the treatment element that is made of a shape memory alloy is configured to directly engage the tissue to cut, ablate, resect, and/or cauterize the tissue.

18. The device of claim 16, wherein in the austenitic state, the treatment element has a pre-set shape having a cross-sectional dimension that is greater than a cross-sectional dimension of the treatment element in the martensitic state.

* * * * *